United States Patent
Surti et al.

(10) Patent No.: US 8,551,139 B2
(45) Date of Patent: Oct. 8, 2013

(54) VISCERAL ANCHORS FOR PURSE-STRING CLOSURE OF PERFORATIONS

(75) Inventors: Vihar C. Surti, Winston-Salem, NC (US); David Desilets, Springfield, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1262 days.

(21) Appl. No.: 11/946,565

(22) Filed: Nov. 28, 2007

(65) Prior Publication Data

US 2008/0132948 A1 Jun. 5, 2008

Related U.S. Application Data

(60) Provisional application No. 60/872,023, filed on Nov. 30, 2006.

(51) Int. Cl.
*A61B 17/04* (2006.01)

(52) U.S. Cl.
USPC ............ 606/232; 606/139; 606/158; 606/151

(58) Field of Classification Search
USPC ................... 606/139–158, 74, 103, 300, 232; 24/128, 129 R, 131 R, 712.1, 712.2
See application file for complete search history.

(56) References Cited

U.S. PATENT DOCUMENTS

| 775,985 A | 11/1904 | McKain |
|---|---|---|
| 1,521,396 A | 12/1924 | Scott |
| 2,199,025 A | 4/1940 | Conn |
| 2,609,155 A | 9/1952 | Fosnaugh |
| 2,880,728 A | 4/1959 | Rights |
| 3,299,883 A | 1/1967 | Rubens |
| 3,470,875 A | 10/1969 | Johnson |
| 3,513,848 A | 5/1970 | Winston et al. |
| 3,556,079 A | 1/1971 | Omizo |
| 3,664,345 A | 5/1972 | Dabbs et al. |
| 3,709,214 A | 1/1973 | Robertson |

(Continued)

FOREIGN PATENT DOCUMENTS

| EP | 1484021 A | 12/2004 |
|---|---|---|
| EP | 1598018 A1 | 11/2005 |
| EP | 1602336 A | 12/2005 |
| EP | 1938760 A1 | 7/2008 |
| EP | 2042105 A2 | 4/2009 |

(Continued)

OTHER PUBLICATIONS

International Preliminary Report on Patentability (PCT/US2007/085769) Jun. 3, 2009.

(Continued)

*Primary Examiner* — Corrine M McDermott
*Assistant Examiner* — Mark Mashack
(74) *Attorney, Agent, or Firm* — Brinks Hofer Gilson & Lione (57) ABSTRACT

Medical devices and related methods for closing a perforation in a bodily wall The medical device generally includes a suture having opposing first and second ends and a set of visceral anchors. Each visceral anchor includes a crossbar having opposing ends and a suture slidably attached thereto. Each visceral anchor is passed through the bodily wall adjacent the periphery of the perforation. The ends of the suture are tensioned to reduce the distance between the visceral anchors and compress the bodily wall around the perforation. The ends of the suture are secured to maintain the compression of the bodily wall and close the perforation.

16 Claims, 7 Drawing Sheets

(56) References Cited

U.S. PATENT DOCUMENTS

| | | | |
|---|---|---|---|
| 3,710,400 A | 1/1973 | Sparks | |
| 3,856,016 A | 12/1974 | Davis | |
| 3,870,048 A | 3/1975 | Yoon | |
| 3,911,923 A | 10/1975 | Yoon | |
| 3,954,108 A | 5/1976 | Davis | |
| 3,967,625 A | 7/1976 | Yoon | |
| 3,989,049 A | 11/1976 | Yoon | |
| 4,022,208 A | 5/1977 | Valtchev | |
| 4,085,743 A | 4/1978 | Yoon | |
| 4,103,680 A | 8/1978 | Yoon | |
| 4,235,238 A | 11/1980 | Ogiu et al. | |
| 4,236,470 A | 12/1980 | Stenson | |
| 4,374,523 A | 2/1983 | Yoon | |
| 4,448,194 A | 5/1984 | DiGiovanni et al. | |
| 4,539,716 A | 9/1985 | Bell | |
| 4,635,638 A | 1/1987 | Weintraub et al. | |
| 4,669,473 A * | 6/1987 | Richards et al. | 606/215 |
| 4,738,740 A | 4/1988 | Pinchuk | |
| 4,749,114 A | 6/1988 | Green | |
| 4,773,420 A | 9/1988 | Green | |
| 4,798,606 A | 1/1989 | Pinchuk | |
| 4,821,939 A | 4/1989 | Green | |
| 4,823,794 A * | 4/1989 | Pierce | 606/232 |
| 4,890,615 A | 1/1990 | Caspari et al. | |
| 4,918,785 A * | 4/1990 | Spinner et al. | 16/428 |
| 4,927,410 A | 5/1990 | Kovacs | |
| 5,015,250 A | 5/1991 | Foster | |
| 5,053,043 A | 10/1991 | Gottesman et al. | |
| 5,059,201 A | 10/1991 | Asnis | |
| 5,084,057 A | 1/1992 | Green et al. | |
| 5,123,914 A | 6/1992 | Cope | |
| 5,203,787 A | 4/1993 | Noblitt et al. | |
| 5,222,508 A | 6/1993 | Contarini | |
| 5,254,126 A | 10/1993 | Filipi et al. | |
| 5,258,000 A | 11/1993 | Gianturco | |
| 5,281,237 A | 1/1994 | Gimpelson | |
| 5,297,536 A | 3/1994 | Wilk | |
| 5,304,184 A | 4/1994 | Hathaway et al. | |
| 5,310,407 A | 5/1994 | Casale | |
| 5,316,543 A | 5/1994 | Eberbach | |
| 5,318,221 A | 6/1994 | Green et al. | |
| 5,320,630 A | 6/1994 | Ahmed | |
| 5,320,632 A | 6/1994 | Heidmueller | |
| 5,333,624 A | 8/1994 | Tovey | |
| 5,336,229 A | 8/1994 | Noda | |
| 5,350,385 A | 9/1994 | Christy | |
| 5,364,408 A | 11/1994 | Gordon | |
| 5,366,460 A | 11/1994 | Eberbach | |
| 5,366,480 A | 11/1994 | Corriveau et al. | |
| 5,368,599 A | 11/1994 | Hirsch et al. | |
| 5,368,601 A | 11/1994 | Sauer et al. | |
| 5,374,275 A | 12/1994 | Bradley et al. | |
| 5,376,096 A | 12/1994 | Foster | |
| 5,389,103 A | 2/1995 | Melzer et al. | |
| 5,391,182 A | 2/1995 | Chin | |
| 5,395,381 A | 3/1995 | Green et al. | |
| 5,397,331 A | 3/1995 | Himpens et al. | |
| 5,403,329 A | 4/1995 | Hinchcliffe | |
| 5,403,342 A | 4/1995 | Tovey et al. | |
| 5,405,072 A | 4/1995 | Zlock et al. | |
| 5,405,354 A | 4/1995 | Sarrett | |
| 5,417,691 A | 5/1995 | Hayhurst | |
| 5,417,699 A | 5/1995 | Klein et al. | |
| 5,423,860 A | 6/1995 | Lizardi et al. | |
| 5,439,469 A | 8/1995 | Heaven et al. | |
| 5,458,131 A | 10/1995 | Wilk | |
| 5,462,558 A | 10/1995 | Kolesa et al. | |
| 5,462,561 A | 10/1995 | Voda | |
| 5,464,426 A * | 11/1995 | Bonutti | 606/232 |
| 5,464,427 A | 11/1995 | Curtis et al. | |
| 5,470,338 A | 11/1995 | Whitfield et al. | |
| 5,476,469 A | 12/1995 | Hathaway et al. | |
| 5,478,353 A | 12/1995 | Yoon | |
| 5,484,451 A | 1/1996 | Akopov et al. | |
| 5,486,197 A | 1/1996 | Le et al. | |
| 5,503,623 A | 4/1996 | Tilton, Jr. | |
| 5,507,754 A | 4/1996 | Green et al. | |
| 5,520,700 A | 5/1996 | Beyar et al. | |
| 5,527,343 A | 6/1996 | Bonutti | |
| 5,531,763 A | 7/1996 | Mastri et al. | |
| 5,549,617 A | 8/1996 | Green et al. | |
| 5,549,631 A * | 8/1996 | Bonutti | 606/232 |
| 5,554,183 A | 9/1996 | Nazari | |
| 5,556,402 A | 9/1996 | Xu | |
| 5,562,683 A | 10/1996 | Chan | |
| 5,562,688 A | 10/1996 | Riza | |
| 5,571,090 A | 11/1996 | Sherts | |
| 5,571,119 A | 11/1996 | Atala | |
| 5,573,540 A | 11/1996 | Yoon | |
| 5,573,543 A | 11/1996 | Akopov et al. | |
| 5,578,044 A | 11/1996 | Gordon et al. | |
| 5,584,835 A | 12/1996 | Greenfield | |
| 5,586,986 A | 12/1996 | Hinchcliffe | |
| 5,609,597 A | 3/1997 | Lehrer | |
| 5,626,590 A | 5/1997 | Wilk | |
| 5,630,824 A | 5/1997 | Hart | |
| 5,643,292 A | 7/1997 | Hart | |
| 5,643,317 A | 7/1997 | Pavcnik et al. | |
| 5,645,552 A | 7/1997 | Sherts | |
| 5,653,717 A | 8/1997 | Ko et al. | |
| 5,662,683 A | 9/1997 | Kay | |
| 5,683,402 A | 11/1997 | Cosgrove et al. | |
| 5,690,656 A | 11/1997 | Cope et al. | |
| 5,693,060 A | 12/1997 | Martin | |
| 5,700,273 A | 12/1997 | Buelna et al. | |
| 5,707,379 A | 1/1998 | Fleenor et al. | |
| 5,709,694 A | 1/1998 | Greenberg et al. | |
| 5,728,113 A | 3/1998 | Sherts | |
| 5,741,277 A | 4/1998 | Gordon et al. | |
| 5,741,278 A | 4/1998 | Stevens | |
| 5,746,751 A | 5/1998 | Sherts | |
| 5,769,862 A | 6/1998 | Kammerer et al. | |
| 5,788,625 A | 8/1998 | Plouhar et al. | |
| 5,792,153 A | 8/1998 | Swain et al. | |
| 5,810,848 A * | 9/1998 | Hayhurst | 606/144 |
| 5,824,010 A | 10/1998 | McDonald | |
| 5,836,955 A | 11/1998 | Buelna et al. | |
| 5,836,956 A | 11/1998 | Buelna et al. | |
| 5,846,253 A | 12/1998 | Buelna et al. | |
| 5,860,990 A | 1/1999 | Nobis et al. | |
| 5,865,791 A | 2/1999 | Whayne et al. | |
| 5,865,836 A | 2/1999 | Miller | |
| 5,891,159 A | 4/1999 | Sherman et al. | |
| 5,902,228 A | 5/1999 | Schulsinger et al. | |
| 5,908,428 A | 6/1999 | Scirica et al. | |
| 5,919,184 A | 7/1999 | Tilton, Jr. | |
| 5,938,668 A | 8/1999 | Scirica et al. | |
| 5,941,900 A * | 8/1999 | Bonutti | 606/232 |
| 5,947,997 A | 9/1999 | Pavcnik et al. | |
| 5,948,000 A | 9/1999 | Larsen et al. | |
| 5,957,937 A | 9/1999 | Yoon | |
| 5,968,078 A | 10/1999 | Grotz | |
| 5,987,707 A * | 11/1999 | DeShon | 24/17 AP |
| 6,010,525 A | 1/2000 | Bonutti et al. | |
| 6,030,365 A | 2/2000 | Laufer | |
| 6,036,699 A | 3/2000 | Andreas et al. | |
| 6,068,648 A | 5/2000 | Cole et al. | |
| 6,071,292 A * | 6/2000 | Makower et al. | 606/158 |
| 6,077,217 A | 6/2000 | Love et al. | |
| 6,086,601 A | 7/2000 | Yoon | |
| 6,086,608 A | 7/2000 | Ek et al. | |
| 6,099,553 A | 8/2000 | Hart et al. | |
| 6,110,183 A | 8/2000 | Cope | |
| RE36,974 E | 11/2000 | Bonutti | |
| 6,156,006 A | 12/2000 | Brosens et al. | |
| 6,200,329 B1 | 3/2001 | Fung et al. | |
| 6,257,163 B1 * | 7/2001 | Carpenter | 114/253 |
| 6,264,677 B1 * | 7/2001 | Simon et al. | 606/232 |
| 6,290,674 B1 | 9/2001 | Roue et al. | |
| 6,293,952 B1 | 9/2001 | Brosens et al. | |
| 6,328,727 B1 | 12/2001 | Frazier et al. | |
| 6,348,059 B1 | 2/2002 | Hathaway et al. | |
| 6,355,050 B1 | 3/2002 | Andreas et al. | |
| 6,416,522 B1 * | 7/2002 | Strecker | 606/143 |

(56) References Cited

U.S. PATENT DOCUMENTS

| | | | |
|---|---|---|---|
| 6,419,669 B1 | 7/2002 | Frazier et al. | |
| 6,423,087 B1 | 7/2002 | Sawada | |
| 6,482,178 B1 | 11/2002 | Andrews et al. | |
| 6,491,707 B2 | 12/2002 | Makower et al. | |
| 6,527,753 B2 | 3/2003 | Sekine et al. | |
| 6,535,764 B2 | 3/2003 | Imran et al. | |
| 6,551,333 B2 | 4/2003 | Kuhns et al. | |
| 6,572,629 B2 | 6/2003 | Kalloo et al. | |
| 6,592,559 B1 | 7/2003 | Pakter et al. | |
| 6,610,026 B2 | 8/2003 | Cragg et al. | |
| 6,626,930 B1 * | 9/2003 | Allen et al. | 606/213 |
| 6,641,557 B1 | 11/2003 | Frazier et al. | |
| 6,652,563 B2 * | 11/2003 | Dreyfuss | 606/232 |
| 6,689,062 B1 | 2/2004 | Mesallum | |
| 6,699,263 B2 | 3/2004 | Cope | |
| 6,712,804 B2 | 3/2004 | Roue et al. | |
| 6,719,763 B2 | 4/2004 | Chung et al. | |
| 6,746,472 B2 | 6/2004 | Frazier et al. | |
| 6,755,843 B2 | 6/2004 | Chung et al. | |
| 6,918,871 B2 | 7/2005 | Schulze | |
| 6,955,643 B2 | 10/2005 | Gellman et al. | |
| 6,966,916 B2 | 11/2005 | Kumar | |
| 6,972,027 B2 | 12/2005 | Fallin et al. | |
| 6,974,466 B2 | 12/2005 | Ahmed et al. | |
| 6,988,987 B2 | 1/2006 | Ishikawa | |
| 6,997,931 B2 | 2/2006 | Sauer et al. | |
| 7,025,756 B2 | 4/2006 | Frazier et al. | |
| 7,033,379 B2 | 4/2006 | Peterson | |
| 7,033,380 B2 | 4/2006 | Schwartz et al. | |
| 7,056,325 B1 | 6/2006 | Makower et al. | |
| 7,060,078 B2 | 6/2006 | Hathaway et al. | |
| 7,060,084 B1 | 6/2006 | Loshakove et al. | |
| 7,076,845 B2 * | 7/2006 | Tylaska et al. | 24/135 N |
| 7,081,124 B2 | 7/2006 | Sancoff et al. | |
| 7,087,073 B2 | 8/2006 | Bonutti | |
| 7,101,862 B2 | 9/2006 | Chochrum et al. | |
| 7,112,207 B2 | 9/2006 | Allen et al. | |
| 7,115,110 B2 | 10/2006 | Frazier et al. | |
| 7,118,583 B2 | 10/2006 | O'Quinn et al. | |
| 7,122,039 B2 | 10/2006 | Chu | |
| 7,122,040 B2 | 10/2006 | Hill et al. | |
| 7,144,401 B2 | 12/2006 | Yamamoto et al. | |
| 7,156,880 B2 | 1/2007 | Evans et al. | |
| 7,157,636 B2 | 1/2007 | Hsieh | |
| 7,166,116 B2 | 1/2007 | Lizardi et al. | |
| 7,175,636 B2 | 2/2007 | Yamamoto et al. | |
| 7,217,279 B2 | 5/2007 | Reese | |
| 7,232,448 B2 | 6/2007 | Battles et al. | |
| RE39,841 E | 9/2007 | Bilotti | |
| 7,273,451 B2 | 9/2007 | Sekine et al. | |
| 7,300,451 B2 | 11/2007 | Crombie et al. | |
| 7,323,004 B2 | 1/2008 | Parahar | |
| 7,326,221 B2 | 2/2008 | Sakamoto | |
| 7,326,231 B2 | 2/2008 | Phillips et al. | |
| 7,331,968 B2 | 2/2008 | Arp et al. | |
| 7,335,221 B2 | 2/2008 | Collier et al. | |
| 7,344,545 B2 | 3/2008 | Takemoto et al. | |
| RE40,237 E | 4/2008 | Bilotti et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,371,244 B2 | 5/2008 | Chatlynne et al. | |
| 7,380,695 B2 | 6/2008 | Doll et al. | |
| 7,380,696 B2 | 6/2008 | Shelton, IV et al. | |
| 7,390,329 B2 | 6/2008 | Westra et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,407,505 B2 | 8/2008 | Sauer et al. | |
| 7,410,086 B2 | 8/2008 | Ortiz et al. | |
| 7,416,101 B2 | 8/2008 | Shelton, IV et al. | |
| 7,416,554 B2 | 8/2008 | Lam et al. | |
| D576,278 S | 9/2008 | Nalagatla et al. | |
| 7,419,080 B2 | 9/2008 | Smith et al. | |
| 7,422,139 B2 | 9/2008 | Shelton, IV et al. | |
| 7,431,694 B2 | 10/2008 | Stefanchik et al. | |
| 7,494,496 B2 | 2/2009 | Swain et al. | |
| 7,601,159 B2 | 10/2009 | Ewers et al. | |
| 7,618,426 B2 | 11/2009 | Ewers et al. | |
| 7,621,925 B2 | 11/2009 | Saadat et al. | |
| 7,622,068 B2 | 11/2009 | Li et al. | |
| 7,641,836 B2 | 1/2010 | Li et al. | |
| 7,674,275 B2 | 3/2010 | Martin et al. | |
| 7,678,135 B2 | 3/2010 | Maahs et al. | |
| 7,691,112 B2 * | 4/2010 | Chanduszko et al. | 606/139 |
| 7,695,493 B2 | 4/2010 | Saadat et al. | |
| 7,704,264 B2 | 4/2010 | Ewers et al. | |
| 7,722,631 B2 * | 5/2010 | Mikkaichi et al. | 606/144 |
| 7,736,378 B2 | 6/2010 | Maahs et al. | |
| 7,736,379 B2 | 6/2010 | Ewers et al. | |
| 7,744,613 B2 | 6/2010 | Ewers et al. | |
| 7,758,598 B2 | 7/2010 | Conlon et al. | |
| 7,833,238 B2 * | 11/2010 | Nakao | 606/151 |
| 7,850,712 B2 * | 12/2010 | Conlon et al. | 606/232 |
| 1,037,864 A1 | 9/2012 | Carlson | |
| 2001/0039426 A1 * | 11/2001 | Makower et al. | 606/153 |
| 2001/0049497 A1 | 12/2001 | Kalloo et al. | |
| 2002/0022851 A1 | 2/2002 | Kalloo et al. | |
| 2002/0116010 A1 | 8/2002 | Chung et al. | |
| 2002/0116011 A1 | 8/2002 | Chee Chung et al. | |
| 2002/0198542 A1 | 12/2002 | Yamamoto et al. | |
| 2003/0045891 A1 | 3/2003 | Yamamoto et al. | |
| 2003/0181924 A1 | 9/2003 | Yamamoto et al. | |
| 2003/0216613 A1 | 11/2003 | Suzuki et al. | |
| 2003/0225312 A1 | 12/2003 | Suzuki et al. | |
| 2004/0002734 A1 | 1/2004 | Fallin et al. | |
| 2004/0097801 A1 | 5/2004 | Mesallum | |
| 2004/0116949 A1 * | 6/2004 | Ewers et al. | 606/167 |
| 2004/0122456 A1 * | 6/2004 | Saadat et al. | 606/157 |
| 2004/0147941 A1 | 7/2004 | Takemoto et al. | |
| 2004/0147958 A1 * | 7/2004 | Lam et al. | 606/232 |
| 2004/0186514 A1 | 9/2004 | Swain et al. | |
| 2004/0220596 A1 | 11/2004 | Frazier et al. | |
| 2004/0225191 A1 | 11/2004 | Sekine et al. | |
| 2004/0243179 A1 | 12/2004 | Foerster | |
| 2004/0249367 A1 * | 12/2004 | Saadat et al. | 606/1 |
| 2004/0249395 A1 * | 12/2004 | Mikkaichi et al. | 606/144 |
| 2005/0004584 A1 | 1/2005 | Franco et al. | |
| 2005/0059984 A1 * | 3/2005 | Chanduszko et al. | 606/151 |
| 2005/0101837 A1 | 5/2005 | Kalloo et al. | |
| 2005/0107664 A1 | 5/2005 | Kalloo et al. | |
| 2005/0113851 A1 | 5/2005 | Swain et al. | |
| 2005/0143762 A1 | 6/2005 | Paraschac et al. | |
| 2005/0149067 A1 | 7/2005 | Takemoto et al. | |
| 2005/0154401 A1 * | 7/2005 | Weldon et al. | 606/139 |
| 2005/0197594 A1 | 9/2005 | Burbank et al. | |
| 2005/0234512 A1 * | 10/2005 | Nakao | 606/232 |
| 2005/0251165 A1 | 11/2005 | Vaughan et al. | |
| 2005/0251166 A1 | 11/2005 | Vaughan et al. | |
| 2005/0251210 A1 * | 11/2005 | Westra et al. | 606/232 |
| 2005/0267479 A1 * | 12/2005 | Morgan et al. | 606/73 |
| 2005/0277945 A1 | 12/2005 | Saadat et al. | |
| 2005/0277957 A1 | 12/2005 | Kuhns et al. | |
| 2005/0277981 A1 | 12/2005 | Maahs et al. | |
| 2006/0002852 A1 | 1/2006 | Saltzman et al. | |
| 2006/0004409 A1 | 1/2006 | Nobis et al. | |
| 2006/0004410 A1 | 1/2006 | Nobis et al. | |
| 2006/0015006 A1 | 1/2006 | Laurence et al. | |
| 2006/0015125 A1 | 1/2006 | Swain | |
| 2006/0020274 A1 | 1/2006 | Ewers et al. | |
| 2006/0020277 A1 | 1/2006 | Gostout et al. | |
| 2006/0025654 A1 | 2/2006 | Suzuki et al. | |
| 2006/0025819 A1 | 2/2006 | Nobis et al. | |
| 2006/0036267 A1 | 2/2006 | Saadat et al. | |
| 2006/0155288 A1 | 7/2006 | Little et al. | |
| 2006/0167482 A1 | 7/2006 | Swain et al. | |
| 2006/0190016 A1 | 8/2006 | Onuki et al. | |
| 2006/0200004 A1 | 9/2006 | Wilk | |
| 2006/0206063 A1 | 9/2006 | Kagan et al. | |
| 2006/0211919 A1 | 9/2006 | Wilk | |
| 2006/0212063 A1 | 9/2006 | Wilk | |
| 2006/0217762 A1 | 9/2006 | Maahs et al. | |
| 2006/0229653 A1 | 10/2006 | Wilk | |

(56) References Cited

U.S. PATENT DOCUMENTS

| | | |
|---|---|---|
| 2006/0235447 A1 | 10/2006 | Walshe |
| 2006/0237022 A1 | 10/2006 | Chen et al. |
| 2006/0237023 A1 | 10/2006 | Cox et al. |
| 2006/0241344 A1 | 10/2006 | Wilk |
| 2006/0241480 A1 | 10/2006 | Wilk |
| 2006/0241570 A1 | 10/2006 | Wilk |
| 2006/0241651 A1 | 10/2006 | Wilk |
| 2006/0241691 A1 | 10/2006 | Wilk |
| 2006/0252997 A1 | 11/2006 | Wilk |
| 2006/0253123 A1 | 11/2006 | Wilk |
| 2006/0253144 A1 | 11/2006 | Mikkaichi et al. |
| 2006/0258909 A1 | 11/2006 | Saadat et al. |
| 2006/0265010 A1 | 11/2006 | Paraschac et al. |
| 2006/0271073 A1 | 11/2006 | Lam et al. |
| 2006/0271101 A1 | 11/2006 | Saadat et al. |
| 2006/0282089 A1 | 12/2006 | Stokes et al. |
| 2006/0286664 A1 | 12/2006 | McAllister et al. |
| 2007/0010835 A1 | 1/2007 | Breton et al. |
| 2007/0049970 A1 | 3/2007 | Belef et al. |
| 2007/0051380 A1 | 3/2007 | Pasricha |
| 2007/0073321 A1* | 3/2007 | Mikkaichi et al. ............ 606/153 |
| 2007/0093858 A1 | 4/2007 | Gambale et al. |
| 2007/0100375 A1 | 5/2007 | Mikkaichi et al. |
| 2007/0100376 A1 | 5/2007 | Mikkaichi et al. |
| 2007/0106313 A1 | 5/2007 | Golden et al. |
| 2007/0112362 A1 | 5/2007 | Mikkaichi et al. |
| 2007/0112425 A1* | 5/2007 | Schaller et al. ............. 623/2.37 |
| 2007/0123840 A1 | 5/2007 | Cox |
| 2007/0150003 A1* | 6/2007 | Dreyfuss et al. ............. 606/232 |
| 2007/0162052 A1 | 7/2007 | Hashimoto et al. |
| 2007/0163585 A1 | 7/2007 | Uesugi et al. |
| 2007/0163596 A1 | 7/2007 | Mikkaichi et al. |
| 2007/0163604 A1 | 7/2007 | Mikkaichi et al. |
| 2007/0167675 A1 | 7/2007 | Miyamoto et al. |
| 2007/0167676 A1 | 7/2007 | Miyamoto et al. |
| 2007/0167967 A1 | 7/2007 | Mikkaichi et al. |
| 2007/0173859 A1 | 7/2007 | Mikkaichi et al. |
| 2007/0191886 A1 | 8/2007 | Dejima et al. |
| 2007/0197864 A1 | 8/2007 | Dejima et al. |
| 2007/0198000 A1 | 8/2007 | Miyamoto et al. |
| 2007/0198033 A1 | 8/2007 | Kalloo et al. |
| 2007/0208360 A1* | 9/2007 | Demarais et al. ............ 606/153 |
| 2007/0213702 A1 | 9/2007 | Kogosaka et al. |
| 2007/0213749 A1 | 9/2007 | Kogosaka et al. |
| 2007/0219411 A1 | 9/2007 | Dejima et al. |
| 2007/0225734 A1 | 9/2007 | Bell et al. |
| 2007/0255100 A1 | 11/2007 | Barlow et al. |
| 2007/0255165 A1 | 11/2007 | Uesugi et al. |
| 2007/0255296 A1 | 11/2007 | Sauer |
| 2007/0260214 A1 | 11/2007 | Mikkaichi et al. |
| 2007/0270629 A1 | 11/2007 | Charles |
| 2007/0270752 A1 | 11/2007 | LaBombard |
| 2007/0270889 A1 | 11/2007 | Conlon et al. |
| 2007/0276424 A1 | 11/2007 | Mikkaichi et al. |
| 2008/0009888 A1 | 1/2008 | Ewers et al. |
| 2008/0015408 A1 | 1/2008 | Paolitto et al. |
| 2008/0021277 A1 | 1/2008 | Stefanchik |
| 2008/0027272 A1 | 1/2008 | Kadykowski |
| 2008/0048002 A1 | 2/2008 | Smith et al. |
| 2008/0058710 A1 | 3/2008 | Wilk |
| 2008/0058865 A1 | 3/2008 | Wilk |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0065157 A1 | 3/2008 | Crombie et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0086153 A1 | 4/2008 | Sakamoto et al. |
| 2008/0097489 A1 | 4/2008 | Goldfarb et al. |
| 2008/0114378 A1 | 5/2008 | Matsushita |
| 2008/0114379 A1 | 5/2008 | Takemoto et al. |
| 2008/0114380 A1 | 5/2008 | Takemoto et al. |
| 2008/0114398 A1 | 5/2008 | Phillips et al. |
| 2008/0119868 A1 | 5/2008 | Sharp et al. |
| 2008/0125804 A1 | 5/2008 | Gostout |
| 2008/0140095 A1 | 6/2008 | Smith et al. |
| 2008/0147116 A1 | 6/2008 | Smith et al. |
| 2008/0154290 A1 | 6/2008 | Golden et al. |
| 2008/0161641 A1 | 7/2008 | Nakazato et al. |
| 2008/0171907 A1 | 7/2008 | Long et al. |
| 2008/0172088 A1 | 7/2008 | Smith et al. |
| 2008/0177304 A1 | 7/2008 | Westra et al. |
| 2008/0183039 A1 | 7/2008 | Long et al. |
| 2008/0185752 A1 | 8/2008 | Cerwin et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228029 A1 | 9/2008 | Mikkaichi et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0249416 A1 | 10/2008 | Sato |
| 2008/0255422 A1 | 10/2008 | Kondoh et al. |
| 2008/0255423 A1 | 10/2008 | Kondo et al. |
| 2008/0255427 A1 | 10/2008 | Satake et al. |
| 2008/0262525 A1 | 10/2008 | Chang et al. |
| 2008/0269566 A1 | 10/2008 | Measamer |
| 2008/0296344 A1 | 12/2008 | Cropper et al. |
| 2008/0300627 A1 | 12/2008 | Measamer et al. |
| 2008/0300629 A1 | 12/2008 | Surti |
| 2008/0319257 A1 | 12/2008 | Sato et al. |
| 2009/0005800 A1 | 1/2009 | Franer et al. |
| 2009/0024163 A1 | 1/2009 | Zeiner et al. |
| 2009/0076527 A1 | 3/2009 | Miyamoto et al. |
| 2009/0088780 A1 | 4/2009 | Shiono et al. |
| 2009/0125039 A1 | 5/2009 | Mikkaichi et al. |
| 2009/0204147 A1 | 8/2009 | Rahmani |
| 2009/0299406 A1 | 12/2009 | Swain et al. |
| 2009/0326561 A1 | 12/2009 | Carroll, II et al. |
| 2009/0326578 A1 | 12/2009 | Ewers et al. |
| 2010/0010457 A1 | 1/2010 | Ewers et al. |
| 2010/0042115 A1 | 2/2010 | Saadat et al. |
| 2010/0042144 A1 | 2/2010 | Bennett |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0174312 A1 | 7/2010 | Maahs et al. |
| 2010/0198192 A1 | 8/2010 | Serina et al. |

FOREIGN PATENT DOCUMENTS

| | | |
|---|---|---|
| WO | WO 0110312 | 2/2001 |
| WO | WO/0158363 | 8/2001 |
| WO | WO 2006/044837 A2 | 4/2006 |
| WO | WO 2008/109087 | 9/2008 |

OTHER PUBLICATIONS

International Search Report/Written Opinion (PCT/US2010/029798) Jun. 6, 2010.

(56) References Cited

OTHER PUBLICATIONS

International Search Report/Written Opinion (PCT/US2010/029738) Jun. 4, 2010.
International Search Report/Written Opinion (PCT/US2009/066566) May 3, 2010.
A. Fritscher-Ravens, Transgastric Endoscopy—A new Fashion, a New Excitement, Article pp. 161-167, Endoscopy 2007—vol. 39, Homerton Hospital, UK.
R.P. Voermans et al., In Vitro Comparison and Evaluation of Seven Gastric Closure Modalities for Natural Orifice Transluminal Endoscopic Surgery (NOTES), Article pp. 595-601, Endoscopy 2008, vol. 40.
Guido M. Sclabas, et al., Endoluminal Methods for Gastrotomy Closure in Natural Orifice TransEnteric Surgery (NOTES), Surgical Innovation, vol. 13, No. 1 pp. 23-30, Mar. 2006.
Emanuel Sporn, et al., Endoscopic Colotomy Closure for Natural Orifice Transluminal Endoscopic Surgery Using a T-Fastener Prototype in Comparison to Convential Laparoscopic Suture Closure, Article Gastrointestinal Endoscopy, pp. 724-730, vol. 68, No. 4, 2008.
David J. Desilets, et al., Loop-Anchor Purse-String Versus Endoscopic Clips for Gastric Closure: A Natural Orifice Transluminal Endoscopic Surgery Comparison Study Using Burst Pressures, Article Gastrointestinal Endoscopy pp. 1225-1230, vol. 70, No. 6, 2009.
E. Sporn, et al., Endoscopic Colotomy Closure After Full Thickness Excision: Comparison of T Fastener with Multiclip Applier, Article Endoscopy, pp. 589-594, vol. 40 2008.
Maria Bergstrom, et al., Early Clinical Experience with a New Flexible Endoscopic Suturing Method for Natural Orifice Transluminal Endoscopic Surgery and Intraluminal Endosurgery, Article Gastrointestinal Endoscopy, pp. 528-533, vol. 67, No. 3, 2008.
Xavier Dray, et al. Air and Fluid Leak Tests after NOTES procedures: A Pilot Study in a Live Porcine Model, Article Gastrointestinal Endoscopy, pp. 513-519, vol. 68, No. 3, 2008.
P.O. Park, et al., Endoscopic Sutured Closure of a Gastric Natural Orifice Transluminal Endoscopic Surgery Access Gastrotomy Compared with open Surgical Closure in a Porcine Model. A Randomized, Multicenter Controlled Trial, Article Endoscopy 2010, vol. 42, pp. 311-317 0.
Search Report & Written Opinion (Jul. 31, 2008) PCT/US2007/085769.

* cited by examiner

VISCERAL ANCHORS FOR PURSE-STRING CLOSURE OF PERFORATIONS

CROSS-REFERENCE TO RELATED APPLICATIONS

This application claims the benefit of U.S. Provisional Application Ser. No. 60/872,023 filed on Nov. 30, 2006, entitled "VISCERAL ANCHORS FOR PURSE-STRING CLOSURE OF PERFORATIONS" the entire contents of which are incorporated herein by reference.

FIELD OF THE INVENTION

The present invention relates generally to visceral anchors for connecting a suture to tissue, and more particularly relates to using visceral anchors and suture to close perforations in tissue.

BACKGROUND OF THE INVENTION

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors (T-anchors) or visceral anchors. An exemplary visceral anchor is disclosed in U.S. Pat. No. 5,123,914, the entire contents of which are incorporated by reference herein. Such visceral anchors have been very successful in medical procedures requiring visceral wall mobilization or wall apposition.

Visceral anchors have also been successfully used in closing perforations, but are not without their drawbacks. For example, when a series of anchors are placed around a perforation, all of the individual sutures connected to the anchors must be collected and connected together. It can often be difficult to properly tension each of the individual sutures to ensure proper approximation of the tissue around the perforation and complete closure thereof. This is especially critical within the gastrointestinal tract, where the travel of bacteria laden fluids outside of the tract may cause unwanted and sometimes deadly infection.

BRIEF SUMMARY OF THE INVENTION

The present invention provides medical devices and related methods for closing a perforation in a bodily wall that provides reliable and complete closure of perforations, while at the same time gives increased versatility and control over perforation closure. One embodiment of a medical device, constructed in accordance with the teachings of the present invention, generally comprises a suture having opposing first and second ends and a set of visceral anchors. Each visceral anchor includes a crossbar having opposing ends, and a suture is slidably attached to the crossbar. The first and second ends of the suture are capable of being independently tensioned for translating the suture relative to each of the visceral anchors and closing the perforation.

According to more detailed aspects, the tensioning of the suture reduces the distance between the visceral anchors to close the perforation in a purse-string fashion. The tensioning of the suture causes compression of the bodily wall around the perforation. Each visceral anchor is positioned on one side of the bodily wall, and first and second ends of the suture are positioned on the opposite side of the bodily wall. The medical device may further include an overtube for delivery of the set of visceral anchors. The overtube has a set of lumens, each lumen receiving a visceral anchor. Portions of the suture located between the visceral anchors extend outside the lumens at a distal end of the overtube. The medical device may also include a set of puncture needles slidably received within the set of lumens, the set of puncture needles receiving the set of visceral anchors therein.

One embodiment of a visceral anchor, constructed in accordance with the teachings of the present invention, generally comprises a crossbar having a passageway. The crossbar has first and second opposing ends and defines a longitudinal axis. The passageway is located between the opposing ends of the crossbar and slidably receives the suture therein. The passageway has an entrance and an exit through which the suture passes. The entrance and exit are spaced apart a distance greater than 0.001 mm and less than 1.0 mm. By providing the entrance and exit of the passageway in close proximity, the leading and trailing portions of the suture may be kept closer together, and the visceral anchor pulled into closer contact with the tissue, while still retaining the ability to translate the suture relative to the anchor. The passageway is also structured to reduce friction between the suture and crossbar.

According to more detailed aspects, the passageway may extend parallel to the longitudinal axis of perpendicular to the longitudinal axis. Preferably, the crossbar is constructed of a cannula having a tubular wall defining a lumen. A first opening in the wall defines the entrance and a second opening in the wall defines the exit. The first opening may take the form a first longitudinal slot formed in the first end of the cannula and the second opening is likewise a second longitudinal slot formed in the second end of the cannula. The tubular wall includes a strip portion extending between the first and second slots. In other embodiments, the visceral anchor further comprises a loop, wherein the passageway is defined between the loop and the crossbar. In some embodiments, the loop is formed by a wire connected to the crossbar and projecting outwardly therefrom. When the crossbar is constructed of a cannula having a tubular wall defining a lumen, the tubular wall defines first and second openings and a first end of the wire is passed through the first opening and a second end of the wire is passed through the second opening. The first and second ends of the wire are secured within the lumen of the cannula. In other embodiments, the loop is formed by a rod connected to the crossbar. When the crossbar is constructed of a cannula, the rod is secured within the lumen of the cannula. The tubular wall will define an opening in communication with the lumen to provide access to the rod. The rod may extend parallel with the longitudinal axis or perpendicular to the longitudinal axis.

According to another aspect of the present invention, a method for closing a perforation in a bodily wall is provided in accordance with the teachings of the present invention. The method utilizes a set of visceral anchors connected to a suture as previously described. Each visceral anchor is passed through the bodily wall adjacent the periphery of the perforation. Each visceral anchor is on a distal side of the bodily wall, while the ends of the suture on a proximal side of the bodily wall. The ends of the suture are tensioned to reduce the distance between the visceral anchors and compress the bodily wall around the perforation. The ends of the suture are secured to maintain the compression of the bodily wall and close the perforation.

According to more detailed aspects, the passing step includes positioning the set of visceral anchors around the perforation to permit closing of the perforation in a purse-string fashion. The passing step preferably includes positioning the set of visceral anchors sequentially around the perforation in a semi-annular or annular shape. Alternatively, the passing step includes positioning the set of visceral anchors sequentially in opposite sides of the perforation. The tensioning steps preferably include independently tensioning the ends of the suture.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
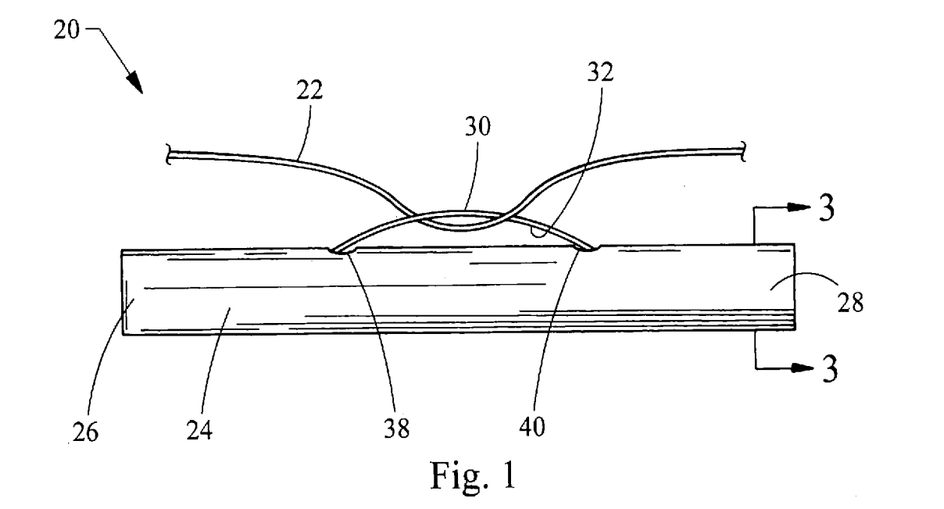
FIG. 1 is a front view of a visceral anchor constructed in accordance with the teachings of the present invention.
Figure 2:
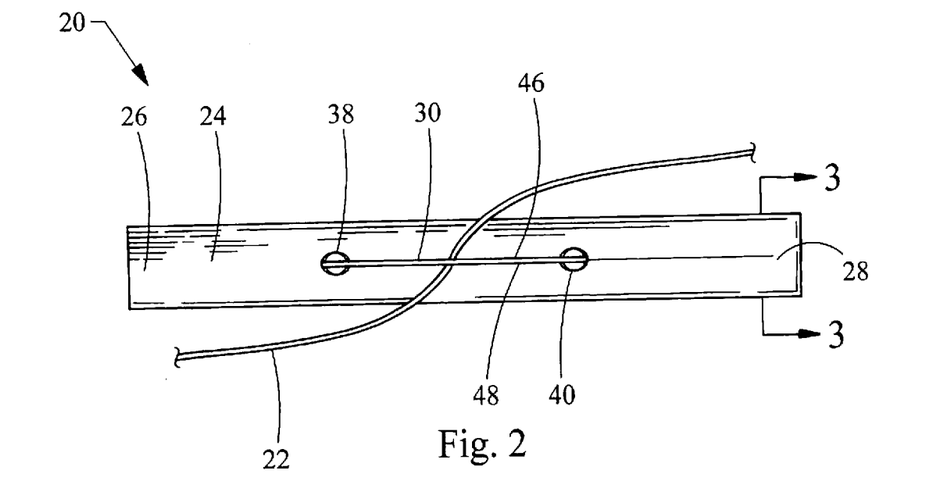
FIG. 2 is a top view of the visceral anchor depicted in FIG. 1.
Figure 3:
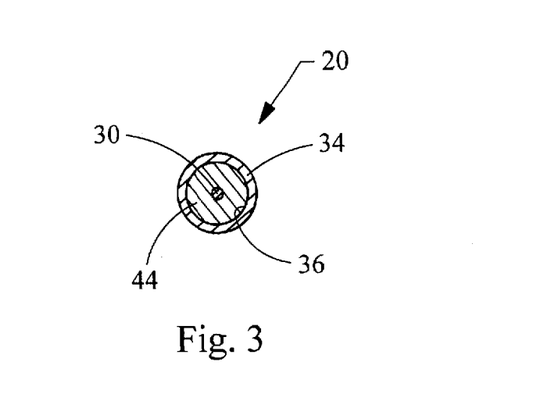
FIG. 3 is a cross-sectional view taken about the line 3-3 in FIG. 1.
Figure 4:
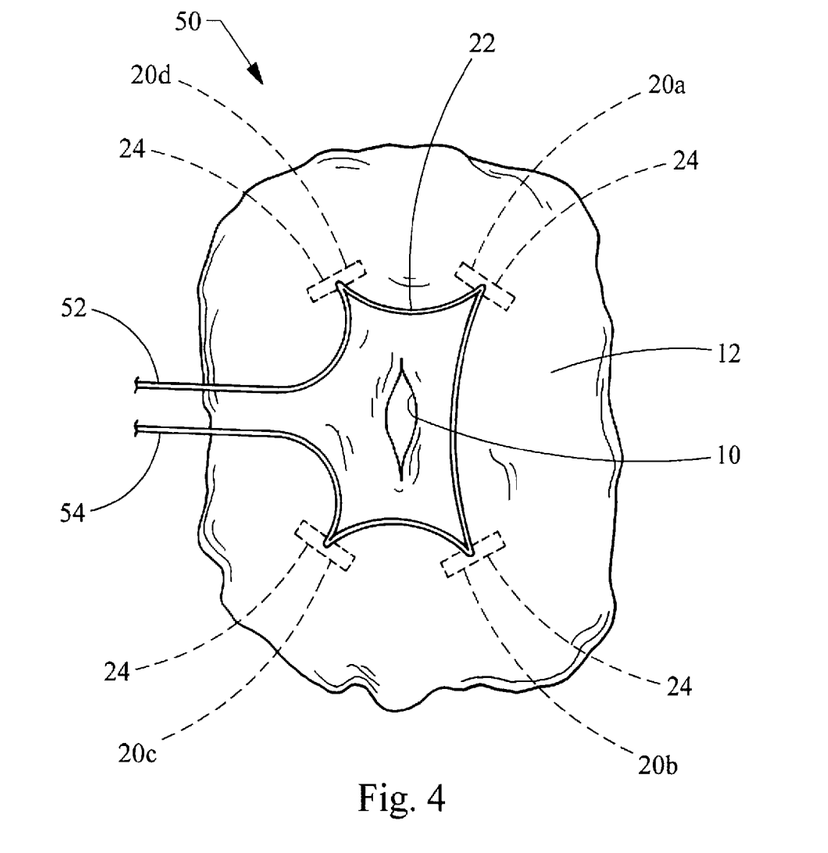
FIG. 4 is a plan view schematically depicting a medical device constructed in accordance with the teachings of the present invention.
Figure 5:
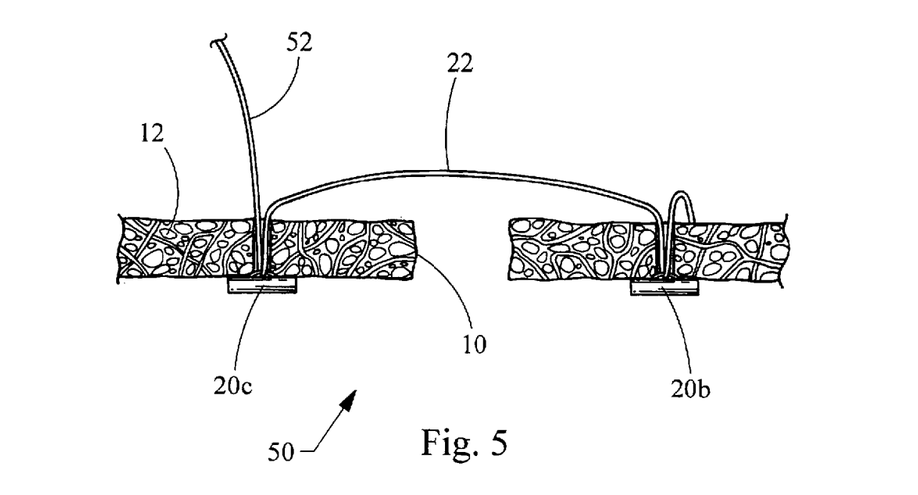
FIG. 5 is a cross-sectional view of the medical device depicted in FIG. 4.

Turning now to the figures, FIGS. 1-3 depict a visceral anchor 20 constructed in accordance with the teachings of the present invention. The anchor 20 is utilized to connect a suture 22 to tissue for closing a perforation 10 in a bodily wall 12 (FIGS. 4 and 5). The anchor 20 generally includes a crossbar 24 having opposing ends 26 and 28. The crossbar 24 is preferably elongated, but may take any form suitable for connecting the suture 22 to the bodily wall 12. A wire 30 connected to the crossbar 24 to form a loop defining a passageway 32 between the wire 30 and crossbar 24. As best seen in FIG. 3, the crossbar 24 is constructed of a cannula having a tubular wall 34 defining a lumen 36. First and second apertures 38, 40 are formed in the tubular wall 34, and the wire 30 passes through the apertures 38, 40. The ends of wire 30 are secured within the lumen 36 of the cannula by welds 44. It will be recognized by those skilled in the art that the wire 30 may be secured to the crossbar 24 using any now known or hereinafter developed attachment means, including mechanical fasteners, adhesives or various welding or soldering techniques.

Notably, the passageway 32 has an entrance 46 and an exit 48 through which the suture 22 passes. The entrance and exit are spaced apart a very short distance so that the leading and trailing portions of the suture 22 may remain in close proximity, allowing the crossbar 24 to be pulled extremely close to the bodily wall 12 and ensuring good compression of the tissue and closure of the perforation 10. Preferably, the entrance and exit are spaced apart a distance less than an outer diameter of the crossbar 24, and more preferably a distance greater than 0.001 mm. and less than 1.0 mm. In this embodiment, the distance is defined by a diameter of the wire 30, and hence the wire 30 having a size in this range is selected for construction of the anchor 20. It will also be seen that the wire 30 results in limited friction between the wire 30 and suture 22, ensuring reliable operation for purse-string type closure of the perforation 10. The wire 30 may also be coating with a hydrophilic coating or other material which aids in the reduction of friction.

Turning now to FIGS. 4-7, the visceral anchors 20 are preferably deployed as a set of anchors 20a, 20b, 20c, 20d linked together by a single suture 22, all of which collectively forms a medical device 50 for closing the perforation 10 in the bodily wall 12. The suture 22 is slidably connected to each of the visceral anchors 20a, 20b, 20c, and 20d, leaving two free ends 52, 54 of the suture 22 which may be independently tensioned to close the perforation 10. As best seen in FIG. 5, the visceral anchors (20b and 20c depicted) are positioned on a distal side of the bodily wall 12, while the majority of suture 22 is positioned on a proximal side of the bodily wall 12, including the suture ends 52, 54. Accordingly, it will be recognized that the medical device 50 operates in a purse-string fashion to close the perforation 10 in the bodily wall, as will be described in more detail below.

Figure 6:
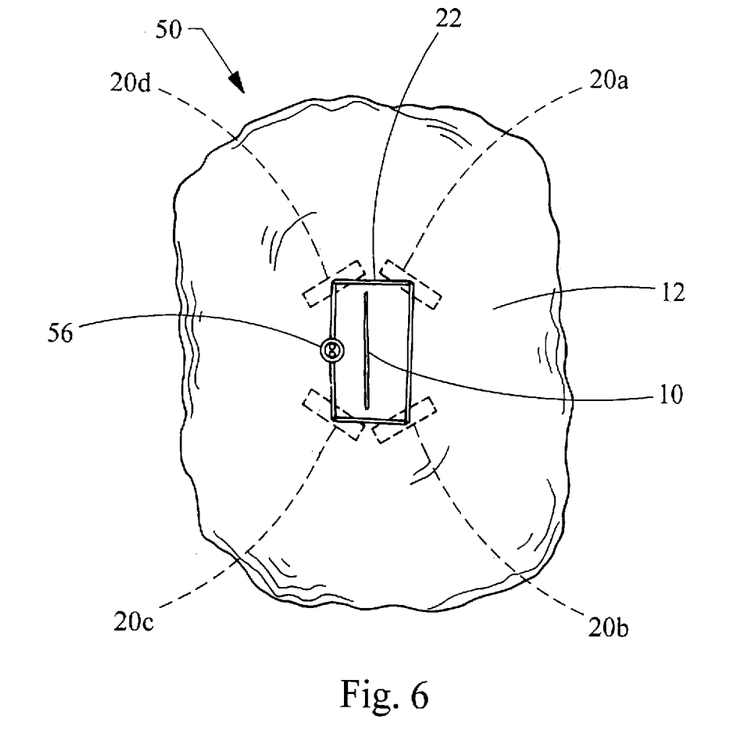
FIG. 6 is a schematic view of the medical device similar to FIG. 4 but showing the medical device closing a perforation.
Figure 7:
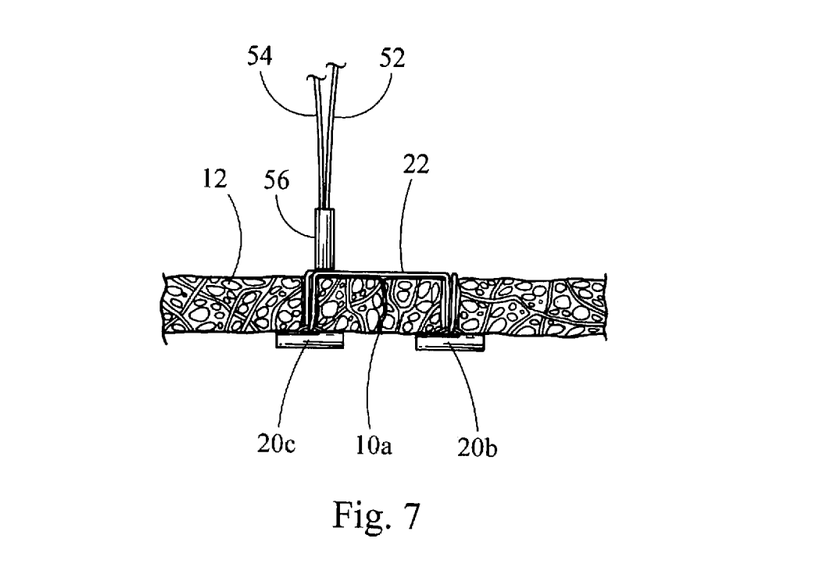
FIG. 7 is a cross-sectional view of the medical device as depicted in FIG. 6.

A method of closing the perforation 10, in accordance with the teachings present invention, includes passing each visceral anchor 20a, 20b, 20c, and 20d through the bodily wall 12 adjacent the periphery of the perforation 10, as shown in FIG. 4. Preferably, the anchors are sequentially positioned around the perforation 10 in a semi-annular or annular shape as shown. The ends 52, 54 of the suture are then tensioned to reduce the distance between the visceral anchors 20a, 20b, 20c, 20d and compress the bodily wall 12 around the perforation 10, as depicted in FIGS. 6 and 7. As best seen in FIG. 7, the ends 52, 54 of the suture 22 are secured to maintain the compression of the bodily wall 10, such as through the use of a suture lock 56. Exemplary suture locks are disclosed in U.S. Patent Application Nos. 60/941,086 and 60/956,575, the disclosures of which are incorporated herein by reference in their entirety. It will be recognized that any now known or future developed method for securing the ends 52, 54 of the suture 22 may be employed, such as knotting, tying, clamps, rivets and the like.

Figure 8:
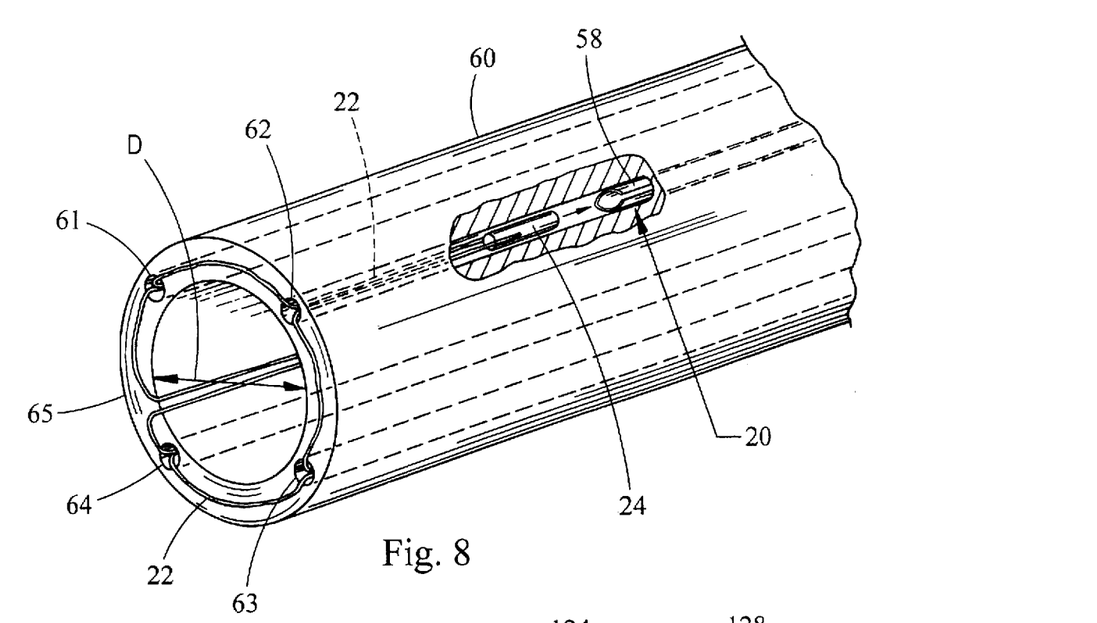
FIG. 8 is a perspective view, partially cutaway, depicting an overtube for deploying the medical device depicted in FIG. 4.

One preferred delivery mechanism optionally forming a portion of the medical device 50 includes an overtube 60 having a set of lumens 61, 62, 63, 64, i.e., one lumen for each visceral anchor 20 that is desired to be deployed. Each lumen 61, 62, 63, 64 extends through a distal end 65 of the overtube 60 and is sized to receive a puncture needled 58 therein. A distal end of the puncture needle 58 receives a visceral anchor 20, and the leading and trailing portions of the suture 22 project distally from each anchor 20. The interconnecting portions of the suture 22 (i.e. between each anchor 20) extend outside of the overtube 60 and along its distal end 65. The free ends 54, 56 of the suture 22 extend proximally along the interior of the overtube 60 (and hence proximally through the bodily lumen) and outside of the body.

The overtube 60 has an inner diameter D that is preferably sized to be about the same size or greater than the largest dimension of the perforation 10 in the bodily wall 12. Accordingly, it will be recognized that the overtube 60 may be positioned against the bodily wall 12 in a location that covers the perforation 10. Each of the puncture needles 58 may be translated distally and passed through the bodily wall 12. A plunger (not shown) is used to expel the visceral anchors 20 from the puncture needles 58 on the distal side of the bodily wall 12. The puncturing needles 58 are then retracted, as is the overtube 60 to leave the crossbars 24 on the distal side of the bodily wall 12, while the suture 22 and its free ends 54,56 remain on the proximal side of the bodily wall 12.

It will be recognized that through use of the overtube 60, the entire set of visceral anchors may be simultaneously deployed, or alternatively may be deployed in various combinations, such as in pairs or individually, and in various sequences as need or desired. It will also be recognized that placement of the set of anchors 20 may be aided by fluoroscopy, ultrasound or visually through the use of medical instruments having imaging capabilities such as an endoscope that is passed through the lumen of the overtube 60. The overtube is preferably constructed of a plastic such as polytetrafluorethylene (PTFE), expanded polytetrafluorethylene (EPTFE), polyethylene ether ketone (PEEK), polyvinylchloride (PVC), polycarbonate (PC), polyamide including nylon, polyimide, polyurethane, polyethylene (high, medium or low density), and elastomers such as Santoprene™, including multi-layer or single layer constructions with or without reinforcement wires, coils or filaments.

Figure 9:
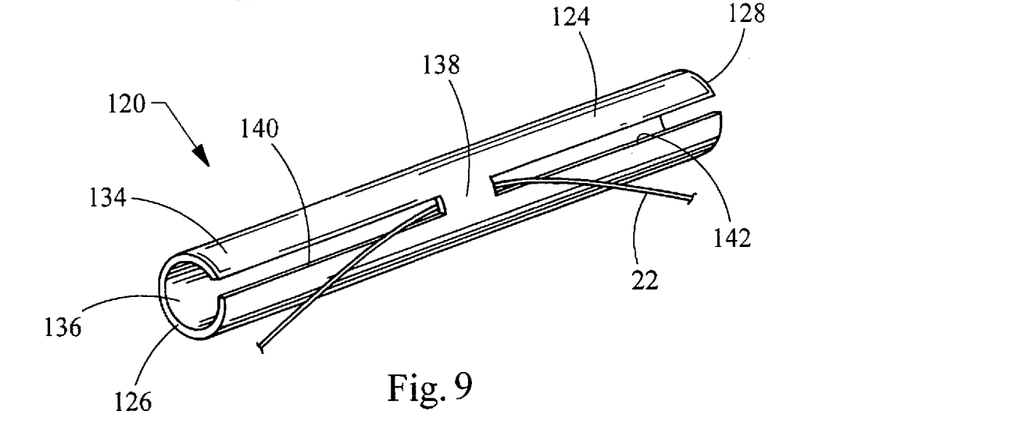
FIG. 9 is a perspective view of an alternate embodiment of a visceral anchor constructed in accordance with the teachings of the present invention.
Figure 10:
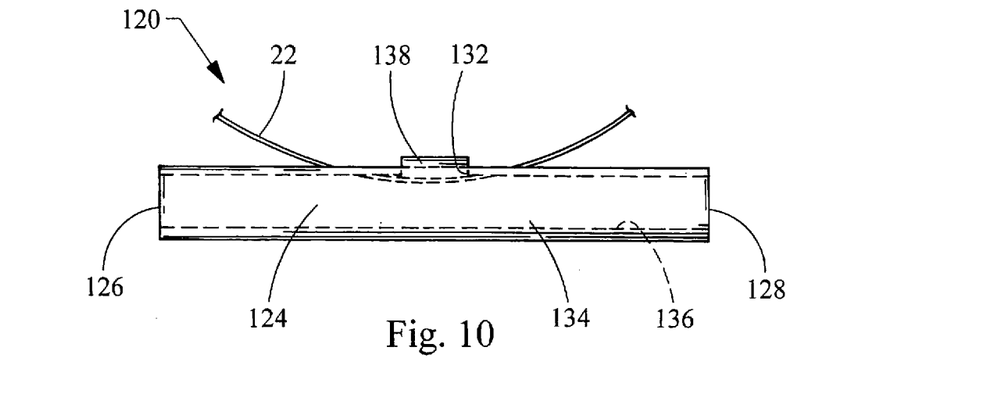
FIG. 10 is a side view of the visceral anchor depicted in FIG. 9.

Turning now to FIGS. 9-14, these figures depict various alternate embodiments of visceral anchors 120, 220, 320 that are constructed in accordance with the teachings of the present invention. In FIGS. 9 and 10, the visceral anchor 120 is again constructed of a crossbar 124 having opposing ends 126, 128 and defining a longitudinal axis. The crossbar 124 is constructed of a cannula having a tubular wall 134 defining an interior lumen 136. In this embodiment, a first slot 140 is formed at the first end 126 of the cannula, and a second slot 142 is formed at the second end 128 of the cannula. The slots 140, 142 extend longitudinally and leave a centrally located strip portion 138 of the cannula. The strip portion 138, in combination with the tubular wall 134, defines a passageway 132 therebetween for receiving a suture 22. The distance between the entrance and exit of the passageway 132 is defined by the length of the strip portion 138.

It will be recognized that the length of strip portion 138 may be sized larger than 1.0 mm, although it may also be smaller. Regardless of the size of the passageway (i.e. between entrance and exit) the passageway is preferably structured to reduce friction between the crossbar and suture, and ensure reliable translation of the anchor relative to the suture. This may be accomplished by eliminating sharp edges, and/or utilizing a hydrophilic coating or other low-friction materials.

Figure 11:
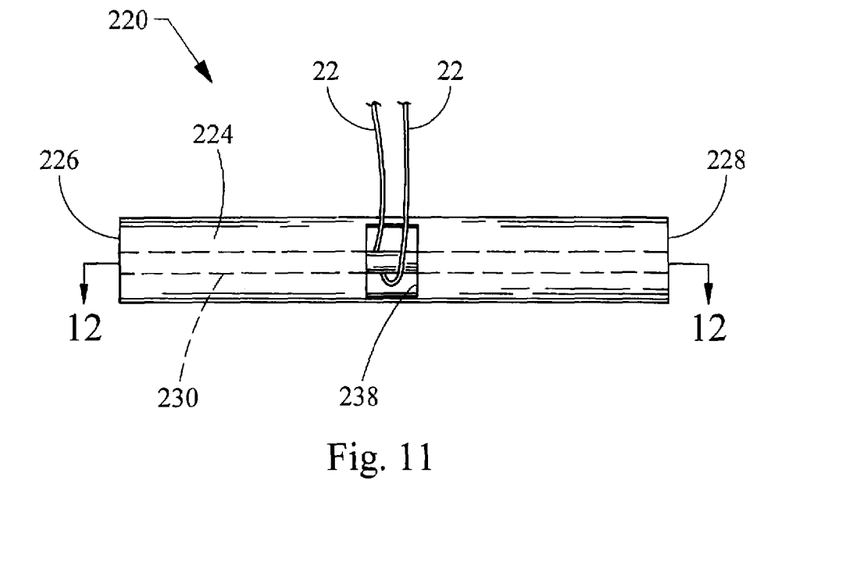
FIG. 11 is a plan view of another alternate embodiment of a visceral anchor constructed in accordance with the teachings of the present invention.
Figure 12:
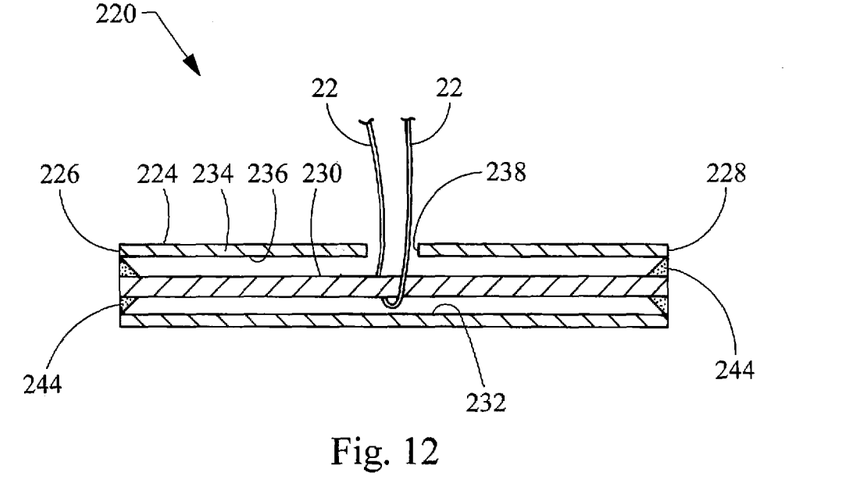
FIG. 12 is a cross-sectional view of the visceral anchor depicted in FIG. 11.

In FIGS. 11 and 12, the visceral anchor 220 includes a crossbar 224 having opposing ends 226, 228 and defining a longitudinal axis. The crossbar 224 is constructed of a cannula having a tubular wall 234 defining an interior lumen 236. In this embodiment, a rod 230 is fitted inside the interior lumen 236. The rod 230 extends parallel to the longitudinal axis and is secured to the ends 226, 228 of the crossbar 224, such as by welds 244. Again, any now known or hereinafter developed connection means may be employed for the rod 230, such as those previously described for the wire 30. An opening 238 is formed in the tubular wall 234 of the crossbar 224 to provide access to the lumen 236 and the rod 230. It will therefore be seen that a passageway 232 is formed by the portion of the lumen 236 located between the rod 230 and tubular wall 234. Here, the distance between the entrance and exit of the passageway 232 is defined by a diameter or width of the rod 230.

Figure 13:
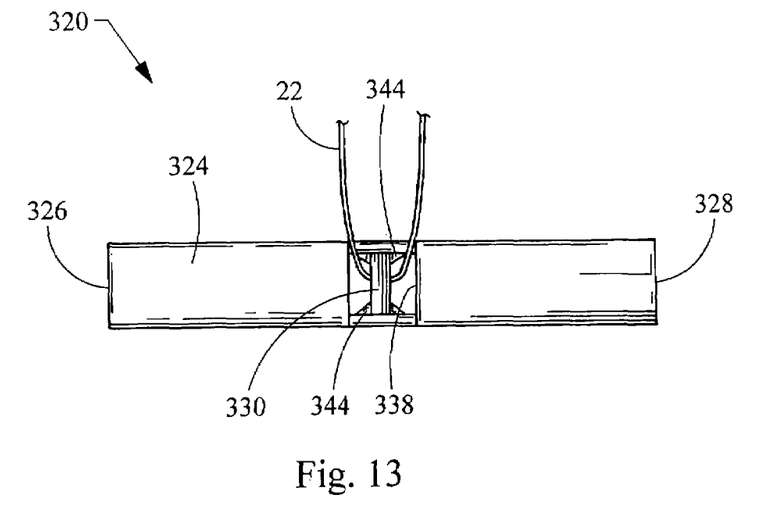
FIG. 13 is a plan view of another alternate embodiment of a visceral anchor constructed in accordance with the teachings of the present invention.
Figure 14:
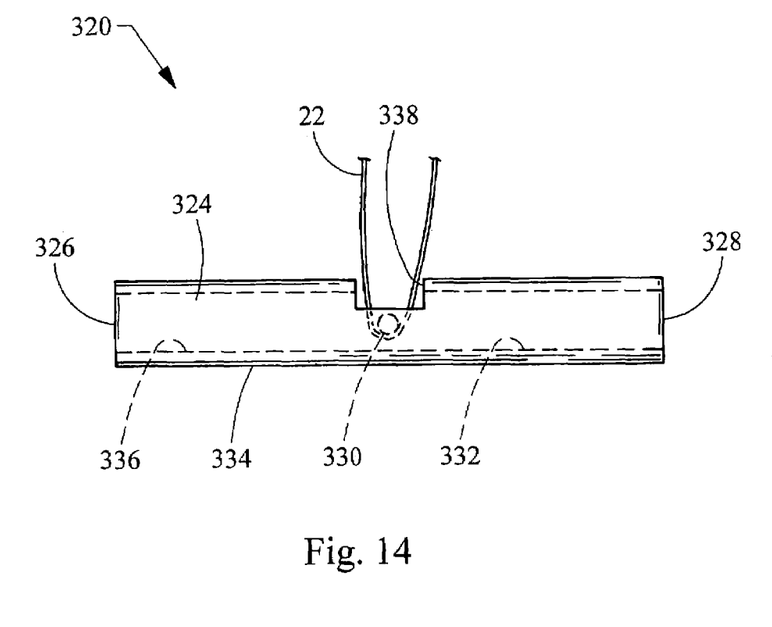
FIG. 14 is a side view of the visceral anchor depicted in FIG. 13.

With reference to FIGS. 13 and 14, yet another embodiment of a visceral anchor 320 includes a crossbar 324 having opposing ends 326, 328 and defining a longitudinal axis. The crossbar 324 is constructed from a cannula having a tubular wall 234 defining a lumen 336. Like the previous embodiment, a rod 330 is again positioned within the lumen 336, and an opening 338 in the tubular wall 334 provides access to the loop and rod 330. However, in this embodiment, the rod 330 is disposed generally perpendicular to the longitudinal axis and is connected to the tubular wall 334, such as by welds 344. Similar to the prior embodiment, a passageway 332 is formed by the portion of the lumen 336 located between the rod 330 and tubular wall 334. The distance between the entrance and exit of the passageway 332 is defined by the diameter or width of the rod 330.

In the previous embodiments a separately formed rod 230, 330 has been depicted as attached to the crossbar 224, 324. However, it will be recognized that the rods or any other loop structures (passageway forming structures) may be integrally and/or unitarily formed with the crossbar, such as by metal injection molding, casting and the like, as well as by material removal techniques such as laser-cutting, blasting, grinding and the like.

Figure 15:
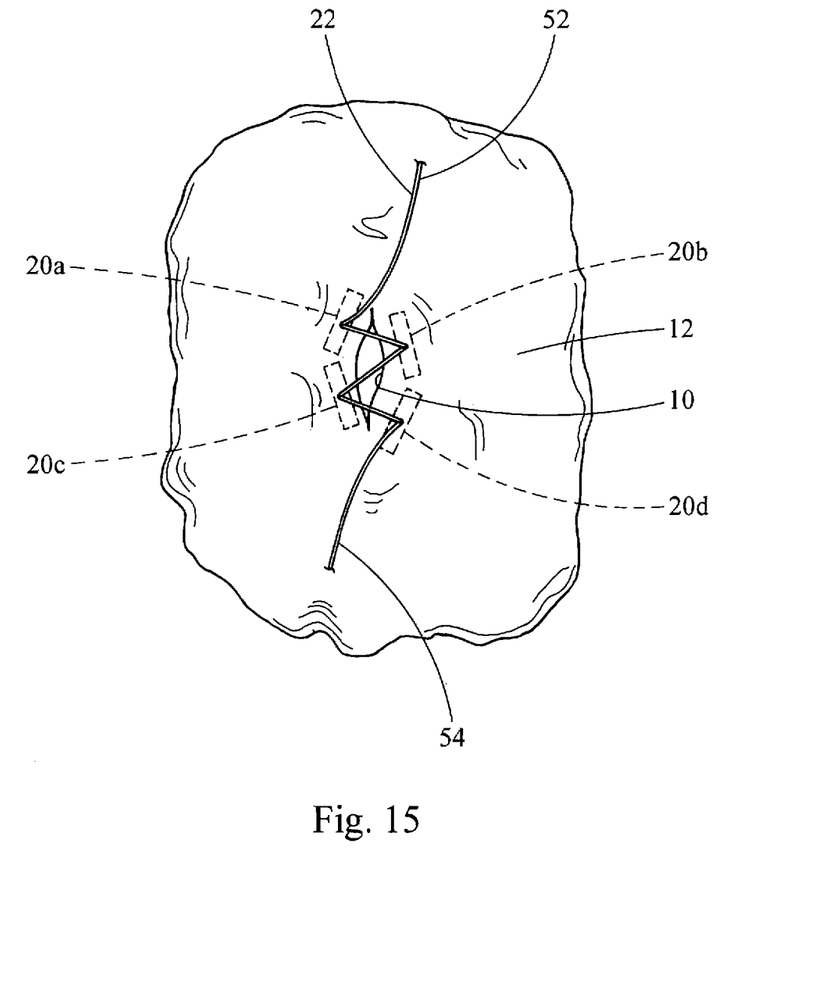
FIG. 15 is a side view of the visceral anchor depicted in FIG. 13.

It will also be recognized by those skilled in the art that not only may numerous types of visceral anchors be employed, but the anchors may also be passed through the bodily wall 12 and orientated relative to one another in numerous ways. For example, in FIG. 15 the set of visceral anchors 20a, 20b, 20c, 20d have been placed on opposing sides of a generally linear perforation 10. More specifically, the visceral anchors 20a, 20b, 20c, 20d have been sequentially positioned on opposite sides of the perforation 10 in a zig-zag configuration. It will be recognized that while semi-annular or zig-zag shapes have been depicted in FIGS. 4 and 15, any number of visceral anchors 20 may be employed, they may be placed in any order and in virtually any configuration. For example, the anchors may criss-cross back and forth and over each other and overlap.

Notably, the ability of each anchor 20 within a set of anchors to slide relative to the suture 22 permits the anchors 20 to be spaced apart any desired distance, providing increased flexibility in their orientation. Likewise, both ends 52, 54 of the suture 22 may be independently adjusted or simultaneously adjusted to draw the anchors 20 closer together and close the perforation through compression of the tissue. The ability to pass sutures completely through the bodily wall 12 while retaining a purse-string type closure improves the compression that may be induced on the bodily wall 12 toward the perforation 10 to ensure a secure and tight closure.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing a perforation in a bodily wall, the medical device comprising:
a suture having opposing first and second ends; and
a set of visceral anchors, each visceral anchor including a crossbar having opposing ends and a wire having first and second ends secured to the crossbar, the crossbar being elongated to define a longitudinal axis, the first and second ends of the wire being longitudinally spaced apart, the crossbar being tubular to define an interior and an exterior, the wire projecting from the interior and extending along the exterior to define the loop, the first and second ends of the wire being secured spaced apart within the lumen to the opposing ends of the crossbar the wire forming a loop through which the suture extends, the suture being slidably attached to each of the crossbars;
the first and second ends of the suture capable of being independently tensioned for translating the suture relative to each of the visceral anchors and closing the perforation.

2. The medical device of claim 1, wherein the tensioning of the suture reduces the distance between the visceral anchors for closing the perforation in a purse-string fashion.

3. The medical device of claim 1, wherein each visceral anchor is positioned on one side of the bodily wall, and wherein the first and second ends of the suture are positioned on the opposite side of the bodily wall.

4. The medical device of claim 1, wherein each visceral anchor includes a passageway between the opposing ends of the crossbar the passageway having an entrance and an exit through which the suture passes, the entrance and exit being spaced apart a distance less than an outer diameter of the crossbar.

5. The medical device of claim 1, further comprising an overtube for delivery of the set of visceral anchors, the overtube having a set of lumens, each lumen receiving a visceral anchor, portions of the suture located between the visceral anchors extending outside the lumens at a distal end of the overtube.

6. The medical device of claim 5, further comprising a set of puncture needles slidably received with the set of lumens, the set of puncture needles receiving the set of visceral anchors therein.

7. The medical device of claim 1, wherein the first and second ends of the wire are welded or soldered to the crossbar.

8. The medical device of claim 1, wherein the crossbar of each visceral anchor in the set of anchors is a single crossbar.

9. A visceral anchor for connecting a suture to tissue, the visceral anchor comprising:
a crossbar having first and second opposing ends, the crossbar defining a longitudinal axis, the crossbar having a tubular wall defining a lumen and an exterior, the tubular wall having first and second openings longitudinally spaced apart; and
a wire having first and second ends extending through the first and second openings in the tubular wall, respectively, and the first and second ends are spaced apart and fixed to the tubular wall within the lumen, the wire projecting out from the tubular wall and extending along the exterior of the tubular wall to form a loop defining a passageway located between the opposing ends of the crossbar, the passageway slidably receiving the suture therein;
the passageway having an entrance and an exit through which the suture passes, the entrance and exit being spaced apart a distance less than an outer diameter of the crossbar.

10. The visceral anchor of claim 9, wherein the entrance and exit are spaced apart a distance greater than 0.001 mm and less than 1 mm.

11. The visceral anchor of claim 9, wherein the passageway extends parallel to the longitudinal axis.

12. The visceral anchor of claim 9, wherein the first and second ends of the wire are secured to the opposing ends of the crossbar within the lumen of the tubular wall.

13. The visceral anchor of claim 9, wherein the wire is coated with a friction reducing material.

14. The visceral anchor of claim 9, wherein the first and second ends of the wire are welded or soldered to the tubular wall.

15. The visceral anchor of claim 9, wherein the first and second ends are fixed to the tubular wall at locations longitudinally spaced apart.

16. The visceral anchor of claim 9, further comprising a suture extending through the passageway of the loop.

* * * * *

UNITED STATES PATENT AND TRADEMARK OFFICE
CERTIFICATE OF CORRECTION

| | | |
|---|---|---|
| PATENT NO. | : 8,551,139 B2 | Page 1 of 1 |
| APPLICATION NO. | : 11/946565 | |
| DATED | : October 8, 2013 | |
| INVENTOR(S) | : Surti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1380 days.

Signed and Sealed this
Fourteenth Day of April, 2015

Michelle K. Lee
*Director of the United States Patent and Trademark Office*